US00PP37354P3

(12) United States Plant Patent
Neu

(10) Patent No.: US PP37,354 P3
(45) Date of Patent: Mar. 31, 2026

(54) ***PELARGONIUM* PLANT NAMED 'KLEPZ24789'**

(50) Latin Name: ***Pelargonium zonale* x *peltatum***
Varietal Denomination: KLEPZ24789

(71) Applicant: KLEMM + SOHN GMBH & CO. KG, Stuttgart (DE)

(72) Inventor: Nina Neu, Weissach im Tal (DE)

(73) Assignee: KLEMM + SOHN GMBH & Co. KG, Stuttgart (DE)

( * ) Notice: Subject to any disclaimer, the term of this patent is extended or adjusted under 35 U.S.C. 154(b) by 0 days.

(21) Appl. No.: 19/187,579

(22) Filed: Apr. 23, 2025

(65) Prior Publication Data

US 2025/0351753 P1 Nov. 13, 2025

(30) Foreign Application Priority Data

May 13, 2024 (CH) ..... 24-3626

(51) Int. Cl.
*A01H 5/02* (2018.01)
*A01H 6/42* (2018.01)

(52) U.S. Cl.
USPC ..... Plt./324
CPC ..... *A01H 6/425* (2018.05); *A01H 5/02* (2013.01)

(58) Field of Classification Search
USPC ..... Plt./324, 330
CPC . A01H 5/02; A01H 5/00; A01H 6/425; A01H 6/42
See application file for complete search history.

(56) References Cited

U.S. PATENT DOCUMENTS

PP29,810 P3 * 11/2018 Feindura ..... Plt./324

OTHER PUBLICATIONS

UPOV Pluto Plant variety Database 20250814 retrieved on Aug. 14, 2025 at https://pluto.upov.int/result, one page. (Year: 2025).*

* cited by examiner

*Primary Examiner* — June Hwu
(74) *Attorney, Agent, or Firm* — Weatherly IP Solutions, LLC; Karen P. Bechtold; James M. Weatherly

(57) ABSTRACT

A new *Pelargonium* plant particularly distinguished by early flowering and flower color that is a vivid red is disclosed.

1 Drawing Sheet

Genus and species: *Pelargonium zonale* x *peltatum.*
Variety denomination: 'KLEPZ24789'.

CROSS REFERENCE TO RELATED APPLICATION

This patent application claims the benefit of priority from Plant Variety Protection Certificate No. 24-3626 as filed on May 13, 2024, in Switzerland, the contents of which are incorporated herein by reference for all it teaches and discloses.

BACKGROUND OF THE NEW PLANT

The present invention comprises a new and distinct variety of *Pelargonium*, botanically known as *Pelargonium zonale* x *peltatum* and hereinafter referred to by the variety name 'KLEPZ24789'. 'KLEPZ24789' originated from a controlled cross in July 2018 in Juja, Kenya between the female *Pelargonium* variety 'KLESATHA' (unpatented) and the proprietary male *Pelargonium* variety 'PZ-2015-5332' (unpatented).

Seeds from the controlled cross were obtained. The seeds were sown and plants were grown for evaluation. A single plant was selected in June 2019 and subsequently named 'KLEPZ24789'. In July 2019 'KLEPZ24789' was first vegetatively propagated by vegetative stem cuttings in Stuttgart, Germany. 'KLEPZ24789' was found to reproduce true to type in successive generations of asexual propagation via stem cuttings in Stuttgart, Germany.

Plant Breeders Rights have been filed for 'KLEPZ24789' in Switzerland in May 2024 (No. 24-3626), the European Union in July 2024 (No. 2024/1380), and Canada on Apr. 22, 2025 (No. 25-12025).

SUMMARY

The following are the most outstanding and distinguishing characteristics of this new variety when grown under normal horticultural practices in Stuttgart, Germany.

1. Early flowering time; and
2. Vivid-red flower color.

DESCRIPTION OF THE PHOTOGRAPH

This new *Pelargonium* plant is illustrated by the accompanying photograph which shows an overall view of the plant in a pot. The photograph is of an approximately 20-week-old plant grown indoors in Stuttgart, Germany. The photograph was taken outdoors in Stuttgart, Germany in July 2024. The colors shown are as true as can be reasonably obtained by conventional photographic procedures.

DESCRIPTION OF THE NEW VARIETY

The following detailed descriptions set forth the distinctive characteristics of 'KLEPZ24789'. Data was collected on 12-week-old plants in Stuttgart, Germany under greenhouse conditions in March 2025. Color references are to The R.H.S. Colour Chart of The Royal Horticultural Society of London (R.H.S.), 5th edition (2007).

Classification:
- *Family*.—Geraniaceae.
- *Botanical*.—*Pelargonium zonale* x *peltatum*.
- *Common*.—*Pelargonium*.
- *Designation*.—'KLEPZ24789'.

Parentage:
- *Female parent*.—'KLESATHA' (unpatented).
- *Male parent*.—'PZ-2015-5332' (unpatented).

Plant:
- *Form*.—Bushy.
- *Habit*.—Mounding.
- *Height* (*from top of soil*).—19.0 cm.
- *Width* (*horizontal plant diameter*).—24.0 cm.
- *Natural flowering season*.—March to October.
- *Propagation type*.—Vegetative by stem cuttings.
- *Time to produce a finished flowering plant*.—12 weeks.
- *Time to initiate and develop roots*.—4 weeks.
- *Root description*.—Fine, dense, white, RHS 158A.
- *Flower type*.—Zygomorphic.

Stems:
- *Quantity of stems per plant*.—4 to 6.
- *Color*.—RHS 144A.
- *Surface texture*.—Pubescent.
- *Stem form*.—Round.
- *Diameter*.—0.7 cm.
- *Length*.—5.0 to 7.0 cm.
- *Internode length*.—1.4 cm.
- *Anthocyanin*.—None.

Leaves:
- *Arrangement*.—Alternate.
- *Shape*.—Reniform.
- *Apex*.—Round.
- *Base*.—Slightly open.
- *Margin*.—Crenate.
- *Surface texture both surfaces*.—Both pubescent.
- *Length*.—7.0 cm.
- *Width*.—8.5 cm.
- *Color*.—Upper surface: RHS 137B. Lower surface: RHS 137D.
- *Zonation*.—No.
- *Depth of Sinus*.—2.0 cm.
- *Petiole*.—Length: 4.6 cm. Diameter: 0.2 cm. Color: RHS 144A. Strength: Medium.
- *Venation pattern*.—Palmate.
- *Venation color*.—Upper surface: RHS 137B. Lower surface: RHS 144A.

Inflorescence:
- *Lastingness of flowers on the plant*.—6 to 8 days.
- *Umbels*.—Quantity of umbels per plant: Twelve-week-old plant: 3 to 7. Twenty-week-old plant: Up to 10. Length: 5.0 cm. Diameter: 8.0 cm.
- *Individual florets of the umbel*.—Average quantity of open florets including closed buds per umbel: 7 to 12. Depth: 2.5 cm. Diameter: 4.7 cm.
- *Fragrance*.—Absent.

Flower buds:
- *Cluster shape*.—Round.
- *Cluster size*.—Length: 0.7 cm. Width: 1.5 cm.
- *Surface texture*.—Pubescent.
- *Bud*.—Height: 0.4 cm. Width: 0.4 cm. Shape: Round. Apex: Acute. Base: Obtuse. Margin: Entire. Color: RHS 144A.

Petals:
- *Flower type*.—Double.
- *Quantity per flower*.—10 to 11.
- *Shape*.—Spatulate.
- *Apex*.—Round.
- *Base*.—Obtuse.
- *Margin*.—Entire.
- *Length*.—2.7 cm.
- *Width*.—1.7 cm.
- *Surface texture*.—Upper surface: Smooth. Lower surface: Smooth.
- *Color of lobes*.—Upper lobes: Upper surface: RHS 46B. Lower surface: RHS 42A. Lower lobes: Upper surface: RHS 46B. Lower surface: RHS 42A.
- *Markings*.—No markings.

Petaloids:
- *Quantity per flower*.—3 to 4.
- *Shape*.—Different shapes crippled.
- *Apex*.—Round or acute or obtuse.
- *Base*.—Obtuse.
- *Margin*.—Entire.
- *Length*.—1.5 cm to 2.0 cm.
- *Width*.—0.3 cm to 0.5 cm.
- *Surface texture*.—Upper surface: Smooth. Lower surface: Smooth.
- *Color*.—Upper surface: RHS 46B. Lower surface: RHS 42A.

Sepals:
- *Number per flower*.—5.
- *Shape*.—Elliptic
- *Apex*.—Acute.
- *Base*.—Obtuse.
- *Margin*.—Entire.
- *Reflexing*.—Absent.
- *Surface texture*.—Upper surface: Smooth. Lower surface: Pubescent.
- *Color*.—Upper surface: RHS 144A at tip, RHS 47A at base. Lower surface: RHS 144A at tip, RHS 47A at base.
- *Length*.—1.0 cm.
- *Width*.—0.3 cm.

Pedicel:
- *Length*.—2.4 cm.
- *Diameter*.—0.1 cm.
- *Color*.—RHS 183B.
- *Surface texture*.—Pubescent.
- *Strength*.—Medium.

Peduncle:
- *Length*.—10 cm.
- *Diameter*.—0.3 cm.
- *Color*.—RHS 144A.
- *Texture*.—Pubescent.
- *Strength*.—Strong.

Reproductive organs:
- *Stamens*.—Quantity per flower: 7 to 10. Anther length: 0.2 cm. Filament length: 1.8 cm. Filament color: RHS NN155D at base, RHS 47B at tip. Pollen amount: Many. Pollen color: RHS N163A.
- *Pistils*.—Number: 1. Stigma color: RHS 45A. Style length: 0.3 cm. Style color: RHS 45A. Ovary arrangement: Central. Ovary color: RHS 144A.

Ovary diameter: 0.2 cm. Ovary length: 0.4 cm. Ovary Texture: Pubescent.

Fruit and seed set: None observed to date.

Disease and pest/insect resistance: None observed to date.

COMPARISON WITH PARENTAL LINES AND KNOWN VARIETY

'KLEPZ24789' is distinguished from its parents as described in Table 1.

TABLE 1

Comparison with Parental Lines

| Characteristic | 'KLEPZ24789' | Female parent | Male parent |
|---|---|---|---|
| Flower time | Early | Late | Medium |
| Vigor | Medium | Medium | Compact |

'KLEPZ24789' can be compared to the commercial variety 'Green Idols Andria' (patent status unknown). Differences between the two varieties are described in Table 2:

TABLE 2

Comparison with Similar Variety

| Characteristic | 'KLEPZ24789' | 'Green Idols Andria' |
|---|---|---|
| Leaf zonation | None | Very weak |
| Flower color | Vivid-red | Red |

I claim:

1. A new and distinct cultivar of *Pelargonium* Plant Named 'KLEPZ24789' as illustrated and described herein.

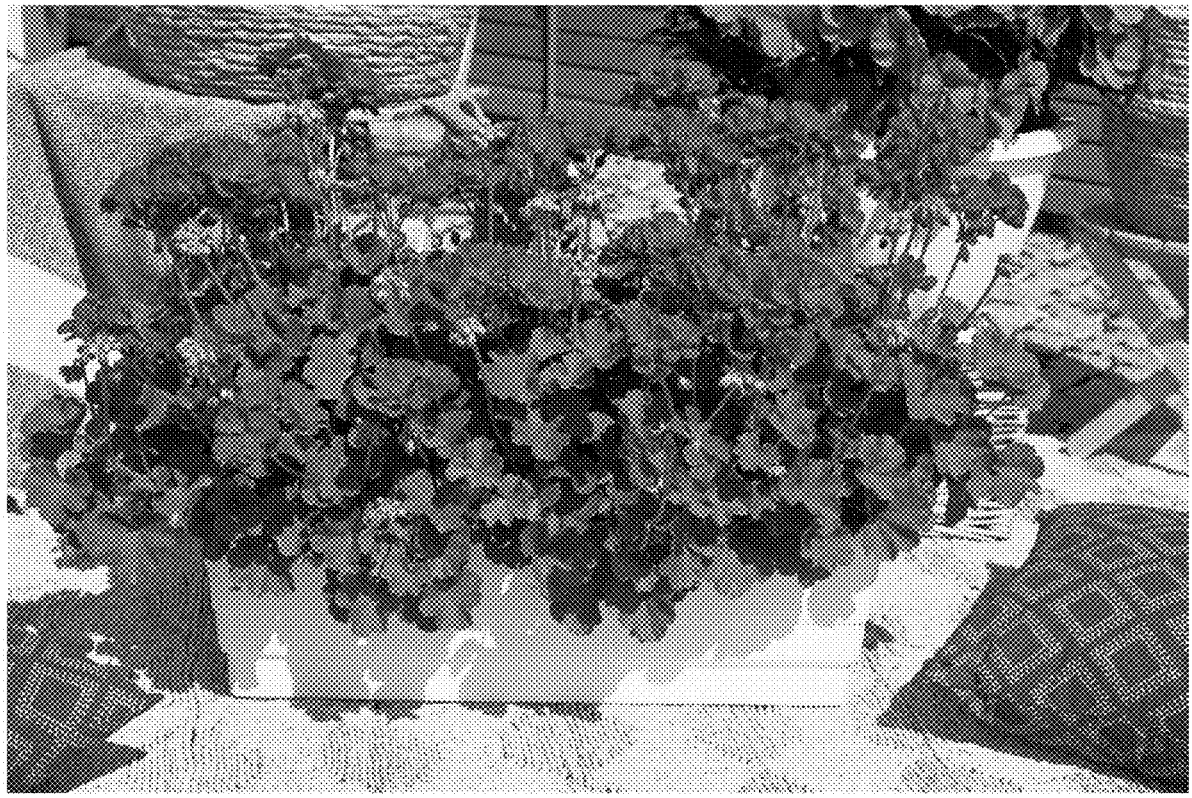

* * * * *